US009995721B2

(12) United States Patent
Hofleitner et al.

(10) Patent No.: US 9,995,721 B2
(45) Date of Patent: Jun. 12, 2018

(54) METHOD FOR DETERMINING A PERFORMANCE INDEX OF A COOKING UTENSIL FOR A PREDETERMINED COOKING TEMPERATURE WITH THE AIM OF ASSESSING NUTRITIONAL GAIN

(71) Applicant: SEB S.A., Ecully (FR)

(72) Inventors: Céline Hofleitner, Annecy (FR); Pascal Cuillery, Faverges (FR)

(73) Assignee: SEB S.A., Ecully (FR)

( * ) Notice: Subject to any disclaimer, the term of this patent is extended or adjusted under 35 U.S.C. 154(b) by 156 days.

(21) Appl. No.: 14/778,365

(22) PCT Filed: Mar. 10, 2014

(86) PCT No.: PCT/FR2014/050536
§ 371 (c)(1),
(2) Date: Sep. 18, 2015

(87) PCT Pub. No.: WO2014/147319
PCT Pub. Date: Sep. 25, 2014

(65) Prior Publication Data
US 2016/0274076 A1    Sep. 22, 2016

(30) Foreign Application Priority Data
Mar. 20, 2013    (FR) ...................... 13 52473

(51) Int. Cl.
*G01N 33/03*    (2006.01)
*A23L 5/10*    (2016.01)
(Continued)

(52) U.S. Cl.
CPC ............ *G01N 33/03* (2013.01); *A23L 1/0107* (2013.01); *A23L 5/11* (2016.08); *A23L 5/12* (2016.08);
(Continued)

(58) Field of Classification Search
CPC ......... G01N 33/03; G01B 21/32; A47J 36/00; A47J 36/02; A47J 36/025; A47J 37/00;
(Continued)

(56) References Cited

U.S. PATENT DOCUMENTS 5,389,440 A * 2/1995 Arpin ...................... C03C 25/30
                                                        428/391
5,532,461 A * 7/1996 Crummenauer ...... A47J 27/002
                                                        126/390.1
(Continued)

FOREIGN PATENT DOCUMENTS

CA    2276295 C    8/2006
FR    2711050 A1    4/1995
(Continued)

OTHER PUBLICATIONS

Mark's NPL, published Apr. 5, 2010, http://www.marksdailyapple.com/forum/forum/the-primal-blueprint-forum-discussion/primal-blueprint-nutrition/6866-cooking-oil-how-much-absorbed-and-consumed.*
(Continued)

*Primary Examiner* — Erik Kashnikow
*Assistant Examiner* — Bryan Kim
(74) *Attorney, Agent, or Firm* — The Webb Law Firm

(57) ABSTRACT

Provided is a method for determining a performance index of a cooking utensil (1a, 1b, 11) for a predetermined cooking temperature with, the aim of assessing nutritional gain, said cooking utensil comprising a bottom (2a, 2b, 10) having a cooking surface (3a, 3b, 10a). The method comprises: a) bringing the cooking surface (3a, 3b, 10a) to said predetermined cooking temperature by using heating means (4), the heating of the surface resulting in a deformation of the bottom (2a, 2b, 10) b) determining a minimum quantity of fat (9, 9a, 9b) necessary to cover the entire cooking surface
(Continued)

(3a, 3b, 10a) of the bottom (2a, 2b, 10) deformed in this way at said predetermined cooking temperature, by pouring the minimum quantity of fat (9, 9a, 9b) necessary to cover the entire cooking surface (3a, 3b, 10a) or by calculating said minimum quantity of fat (9, 9a, 9b) necessary to cover the entire cooking surface (3a, 3b, 10a) by recreating the cooking utensil (11) deformed in this way by means of a computer equipped with a computer assisted design software program, said minimum quantity of fat (9, 9a, 9b) making it possible to define the performance index of the cooking utensil (1a, 1b, 11) for a predetermined cooking temperature.

11 Claims, 3 Drawing Sheets

(51) Int. Cl.
| | |
|---|---|
| *A47J 27/00* | (2006.01) |
| *A47J 36/00* | (2006.01) |
| *A47J 37/10* | (2006.01) |
| *A23L 1/01* | (2006.01) |
| *G01B 21/32* | (2006.01) |
| *A47J 36/02* | (2006.01) |

(52) U.S. Cl.
CPC ............. *A47J 27/00* (2013.01); *A47J 36/00* (2013.01); *A47J 37/10* (2013.01); *G01B 21/32* (2013.01); *A23V 2002/00* (2013.01); *A47J 36/02* (2013.01); *A47J 36/025* (2013.01); *A47J 37/105* (2013.01)

(58) Field of Classification Search
CPC ........ A47J 37/10; A47J 37/105; A47J 37/108; A47J 27/00; A47J 27/002; A23L 5/11; A23L 5/12
USPC .................. 73/87, 149, 169, 863.11, 866
See application file for complete search history.

(56) References Cited

U.S. PATENT DOCUMENTS

| | | | | |
|---|---|---|---|---|
| 7,761,971 | B2* | 7/2010 | Cheng .................. | A47J 27/002 29/505 |
| 8,863,653 | B2 | 10/2014 | Bonnel et al. | |
| 2004/0156954 | A1* | 8/2004 | Maheshwari .......... | A21D 13/31 426/97 |
| 2005/0153022 | A1* | 7/2005 | Schilling ............. | A47J 37/1228 426/92 |
| 2005/0186316 | A1* | 8/2005 | Maruyama ............. | A21D 8/047 426/549 |
| 2006/0196877 | A1* | 9/2006 | Droese .................. | A47J 27/002 220/573.3 |
| 2010/0224636 | A1 | 9/2010 | Etheridge et al. | |
| 2016/0278562 | A1* | 9/2016 | Kim ...................... | A47J 27/002 |

FOREIGN PATENT DOCUMENTS

| | | |
|---|---|---|
| FR | 2780626 A1 | 1/2000 |
| FR | 2919484 A1 | 2/2009 |

OTHER PUBLICATIONS

Seasoned Advice NPL, published Jul. 18, 2010, https://cooking.stackexchange.com/questions/1590/how-do-you-figure-out-how-much-oil-to-use-for-pan-frying.*
Seasoned Advice Heat NPL, published Jul. 22, 2010, https://cooking.stackexchange.com/questions/2690/do-you-heat-the-pan-first-then-add-oil-or-put-the-oil-in-and-heat-up-with-the.*
Seasoned Advice Pan NPL, post published Apr. 14, 2011, answer published Apr. 15, 2011, https://cooking.stackexchange.com/questions/14044/how-does-thermal-shock-affect-pans-made-of-different-materials.*

* cited by examiner

METHOD FOR DETERMINING A PERFORMANCE INDEX OF A COOKING UTENSIL FOR A PREDETERMINED COOKING TEMPERATURE WITH THE AIM OF ASSESSING NUTRITIONAL GAIN

CROSS-REFERENCE TO RELATED APPLICATIONS

This application is the United States national phase of International. Application No. PCT/FR2014/050536 filed Mar. 10, 2014, and claims priority to French Patent Application No. 1352473 filed Mar. 20, 2013, the disclosures of which are hereby incorporated in their entirety by reference.

Field of the Invention

This invention pertains to the field of cooking utensils, and more specifically a method for determining a performance index of a cooking utensil for a predetermined cooking temperature with the aim of assessing nutritional gain, particularly based on the deformation of the bottom of the cooking utensil. The invention aims to show the relationship between the nutritional gain from cooking done in cooking utensils and the concavity of the bottom of these cooking utensils. The invention therefore pertains to all cooking utensils designed to cook food, such as frying pans.

Description of Related Art

The manufacture of cooking utensils for cooking food, such as frying pans, for example, is such that this utensil has, after manufacture, a concave bottom. Indeed, a cooking utensil with a convex bottom would cause a lack of stability in that utensil. When the cooking utensil is heated, it is subjected to significant temperature variations, which result in expansion and deformation phenomena. The bottom of the cooking utensil may then change concavity, or even become convex while cooking food, this change in shape being a function, firstly, of its concavity after manufacture and, secondly, of the design of the bottom of the cooking utensil. The applicant has previously developed cooking utensils for cooking food, with technical characteristics that minimize, as much as possible, the deformation of the bottoms of these utensils during cooking. Such cooking utensils are described, for example, in published patent application numbers FR 2 711 050, FR 2 780 626 and FR 2 919 484.

Experts in the field have also developed methods for measuring the concavity of cooking utensils, both when cold and during cooking, and even after aging. Thus, for example, one can measure the concavity of the bottom of the utensil when cold using a comparator. The concavity of the bottom of the utensil can be measured during cooking using a comparator and a thermocouple. The profile of the bottom of the utensil can also be measured with a laser.

Experts in the field also developed cooking utensils comprising a non-stick coating on the interior surface of the bottom. Nevertheless, it remains true that when cooking certain foods, such as potatoes prepared in a frying pan or sauté pan, for example, the cook still uses fat, which is a real technological tool for successful cooking that improves the organoleptic quality of the food being prepared or cooked. From a nutritional standpoint, however, limiting consumption of fat to between 35% and 40% of daily calorie intake is recommended.

The purpose of this invention is to determine a performance index of a cooking utensil for a predetermined cooking temperature and to characterize the nutritional gain achieved by controlling the flatness of the bottom of cooking utensils while cooking food, in correlation to the organoleptic quality sought by the cook when cooking these foods.

SUMMARY OF THE INVENTION

To this end, the invention pertains to a method of determining a performance index of a cooking utensil for a predetermined cooking temperature, with the aim of assessing nutritional gain, said cooking utensil having a bottom with a cooking surface, characterized in that it includes the following steps:

a) Bringing the cooking surface to said predetermined cooking temperature using a heating means, the heating of the surface resulting in a deformation of the bottom, b) Determining a minimum quantity of fat necessary to cover the entire cooking surface of the bottom deformed in this way at said predetermined cooking temperature by pouring in the minimum quantity of fat necessary to cover the entire cooking surface or by calculating said minimum quantity of fat necessary to cover the entire cooking surface by recreating the cooking utensil deformed in this way by means of a computer equipped with a computer assisted design software program, said minimum quantity of fat making it possible to define the performance index of the cooking utensil for a predetermined cooking temperature.

These steps are performed for a sample group of cooking utensils for cooking food, these cooking utensils being of the same type, such as frying pans with a diameter of 26 cm, for example, from various manufacturers.

Thus, the performance index of the cooking tool for a predetermined cooking temperature is determined by the minimum quantity of fat. The best performance index for a predetermined cooking temperature is obtained with the cooking tool using the lowest minimum quantity of fat. The minimum quantity of fat is directly related to the deformation of the bottom.

In one preferred method of implementation, to perform step (b), the method below is followed:

i. A quantity of fat is poured in, corresponding to a liquid volume of 1 mm thick with a surface area equal to a flat disc equivalent to the cooking surface, ii. The fat is allowed to stabilize at the temperature and spread over the cooking surface of the bottom, iii. A residual cooking surface not covered by the fat is measured, and a quantity of fat is poured in, corresponding to a liquid volume of 1 mm thick with a surface area equal to a flat disc equivalent to the residual cooking surface, iv. Steps (ii) and (iii) are repeated until the entire cooking surface of the bottom of the cooking utensil is covered.

Thus, the sum of the quantities of fat poured into the frying pan determines the minimum quantity of oil to cover the entire bottom of the cooking tool.

In one implementation variant, in this preferred method, the cooking utensil is created using computer assisted design and the minimum quantity of fat in a liquid state necessary to cover the bottom of the cooking utensil is graphically represented, and then the mass properties of the object created using computer assisted design are analyzed in order to calculate said quantity of liquid necessary for cooking.

Advantageously, in step (a) the predetermined cooking temperature chosen is that of potatoes, on the order of 180 to 200° C.

The choice of the predetermined cooking temperature corresponds to the choice of a food for cooking that is preferably oriented toward foods or recipes that are commonly cooked and that require the addition of fat. Ideally, a food cooked by pan frying—or in other words, with a thin film of fat in a liquid state when heated—would be chosen, as opposed to deep frying, where the food is plunged into liquid fat. Thus, in a preferred and non-limiting manner, the food chosen for cooking is potatoes, either in pieces, rounds or whole, depending on their size, for making a recipe of sautéed potatoes.

In one preferred and non-limiting method of implementation, the fat is cooking oil. One could also consider using butter or something similar, or even beef fat, among others.

Advantageously, the method comprises the following steps:
a) Cooking the food in the cooking utensil and quantifying the fat absorbed by the cooked food;
b) Determining the percentage of fat absorbed with respect to the dry matter of the cooked food.

In one preferred and non-limiting method of implementation of step (c), the mass ($m_{uc}$) of the cooking utensil, the mass ($m_{mg}$) of the fat used, the mass ($m_{ac}$) of the raw food, the mass ($m_{ap}$) of the prepared food, the mass ($m_{uc+rmg}$) of the cooking utensil and the residual fat once the prepared food is removed from the cooking utensil are measured, and the mass ($m_{mga}$) of the fat absorbed by the prepared food is deduced from this.

Advantageously, the percentage of fat absorbed with respect to the dry matter of the cooked food is determined using the formula $Tx_{mga/ms} = m_{mga}/m_{ac}/Tx_{ms}$, where $Tx_{ms}$ is the percentage of dry matter of the food.

Preferably, the method comprises a step to measure the deformation of the bottom of the cooking utensil at the predetermined cooking temperature after step (a), and in step (d) the percentage of fat absorbed with respect to the dry matter of the cooked food is determined as a function of the deformation of the cooking utensil.

Various techniques for measuring the deformation of the bottom, whether or not they are known to the expert in the field, can be used within the scope of this invention. In a preferred and non-limiting manner, the deformation of the bottom of the cooking utensil at a predetermined cooking temperature is measured in accordance with Standard XP D21-503.

In one preferred way of implementing the method described in the invention, the cooking utensil is a frying pan. One could imagine implementation variants with other cooking utensils for cooking food, such as a sauté pan, a saucepan or a stockpot.

BRIEF DESCRIPTION OF THE DRAWINGS

The description below pertains to a preferred way of implementing the method described in the invention, based on the drawings, in which.

DETAILED DESCRIPTION OF THE INVENTION

In this preferred way of implementing the method described in the invention, the cooking utensil used is a frying pan. However, the method described in the invention can be implemented with other cooking utensils for cooking food requiring the use of fat to properly achieve said cooking, said cooking utensils being subject to concave deformation during cooking. A saucepan or sauté pan, for example.

In the invention, the method for determining a performance index of a cooking utensil for a predetermined cooking temperature with the aim of assessing nutritional gain comprises the following steps:
a) Bringing the cooking surface to said predetermined cooking temperature using a heating means, the heating of the surface causing a deformation of the bottom,
b) Determining a minimum quantity of fat necessary to cover the entire cooking surface of the bottom, deformed in this way, at said predetermined cooking temperature, by pouring in the minimum quantity of fat necessary to cover the entire cooking surface or by calculating said minimum quantity of fat necessary to cover the entire cooking surface by recreating the cooking utensil, deformed in this way, using a computer equipped with computer assisted design software.

A frying pan that is brought to a heating or cooking temperature undergoes significant temperature variations, which result in expansion and deformation phenomena. Because these temperatures are not homogenous, they cause non-homogenous expansions and force the material of the frying pan to deform. The same is true for the other cooking utensils.

Consequently, the frying pan's concavity can be accentuated or even become convex when it is subjected to heating, as this deformation depends on the concavity of the frying pan after manufacture and the technical characteristics of manufacturing the frying pan, particularly those pertaining to the bottom of the frying pan (material, deformation-resistant ridges, stamping, etc.). Thus we see, for example, that a first frying pan (1a) illustrated in FIG. 1 has a bottom (2a) with very slight concavity, which means that the bottom (2a) remains almost flat when heated. Whereas, a second frying pan (1b) illustrated in FIG. 2 has a bottom (2b) with very pronounced concavity when heated.

Figures 1, 2:
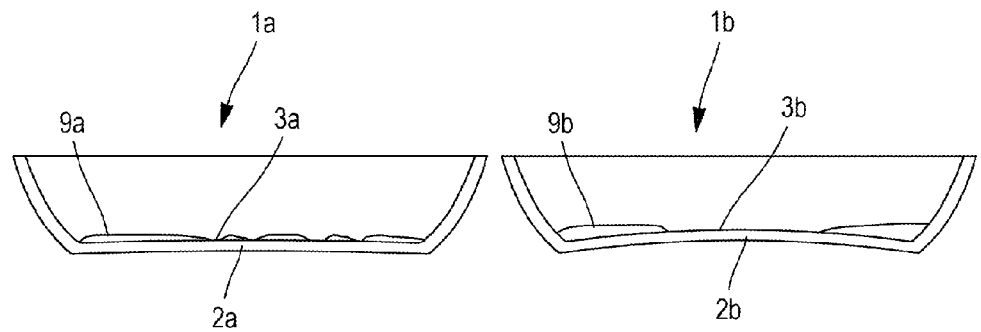
FIGS. 1 and 2 show two cooking utensils for cooking food, the bottoms of which are slightly concave and significantly concave, respectively.

Step (b) of the method described in the invention consists of determining the minimum quantity of fat to completely cover the bottom (2a, 2b) of the frying pan (1a, 1b). In the method of implementation described, the fat used is oil. As can be seen in FIGS. 1 and 2, the distribution of oil is completely different from one frying pan to the other, based on the concavity of the bottom. Regarding the frying pan (1a) in FIG. 1, which has a bottom (2a) with very slight concavity, the oil (9a) is adequately distributed over the entire cooking surface (3a). On the contrary, for the frying pan (1b) in FIG. 2, which has a bottom (2b) with significant concavity, the oil (9b) is located around the edge of the cooking surface (3b). It is therefore understood that in order to have a thin film of oil over the entire cooking surface (3a, 3b), the quantity of oil will be different between the first frying pan (1a) and the second frying pan (1b).

Figure 3:
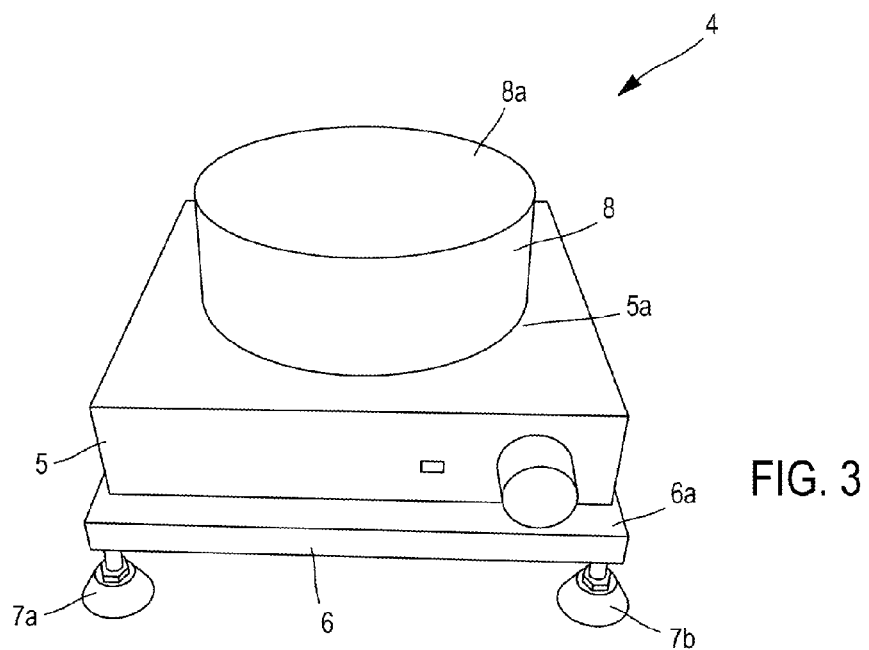
FIG. 3 depicts a means of determining the minimum quantity of oil to cover a hot frying pan.

In order to determine the minimum quantity of oil necessary to cover the cooking surface of the frying pan when hot, a heating means (4), illustrated in FIG. 3, is used, comprising a heat source (5) positioned on a support (6) with feet (7a, 7b), configured so that the upper surface (6a) of said support (6) can be adjusted to be level. The heat source is, for example, a hot plate, with a focus (5a) that is 21 cm in diameter. On this focus (5a) an aluminum block (8) is positioned that is compliant with Standard NF EN 12983-1. This block is made to be level and flat by making adjustments to the support (6). A thermocouple (not depicted), connected to a regulator unit, is inserted into the upper portion of the aluminum block (8).

In addition, frying pans (1a, 1b) that are 26 cm in diameter are used, which are positioned on the top surface (8a) of this aluminum block (8).

The predetermined cooking temperature is that of potatoes, on the order of 180 to 200° C. For the chosen frying pans, the rated temperature is established at 235° C. Once the aluminum block (8) has reached the rated temperature of 235° C., the frying pan is centered on top. As soon as the temperature at mid-radius of the cooking surface has reached 180° C., the next steps are followed:

i. A quantity of oil corresponding to a liquid volume of 1 mm thick and a surface area equal to a flat disc equivalent to the cooking surface (10a) is poured in,
  ii. The oil is allowed to stabilize at the temperature and spread over the cooking surface (3a, 3b, 10a) of the bottom (2a, 2b, 10),
  iii. A residual cooking surface not covered by the oil is measured, and an additional quantity of oil is poured in, corresponding to a liquid volume of 1 mm thick and a surface area equal to a flat disc equivalent to the residual cooking surface,
  iv. Steps (ii) and (iii) are repeated until the entire cooking surface (10a) of the bottom (10) of the cooking utensil (11) is covered.

Figure 4:
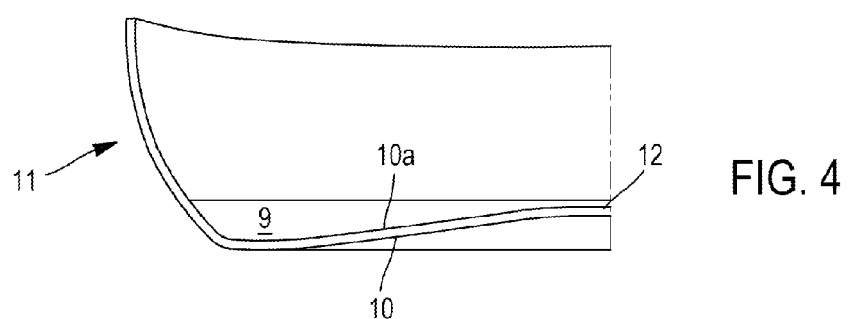
FIG. 4 depicts a partial cross-section of a frying pan, in which oil is covering the bottom.

Thus, the sum of the quantities of oil poured into the frying pan determines the minimum quantity of oil to completely cover the bottom (2a, 2b); the oil (9) completely covering the cooking surface (10a) of the bottom (10) of the frying pan (11), as illustrated in FIG. 4. At the end of this step, the frying pan with the oil (9) covering the bottom (10) is weighed. The mass of oil necessary to cover the cooking surface is then calculated as the difference between the mass of the frying pan containing the oil and the mass of the frying pan when empty, which is how the following formula was derived:

$$\text{mass}_{oil} = \text{mass}_{pan+oil} - \text{mass}_{empty\ pan}$$

Of course, this mass of oil represents the minimum quantity of fat.

Other methods may be considered for determining this minimum quantity of fat necessary to cover the cooking surface of the frying pan. Thus, it is possible to graphically represent, through computer assisted design ("CAD"), the minimum quantity of oil (9) to cover the cooking surface (10a) of the bottom (10) of the frying pan (11) when hot. The bottom (10) is considered covered when the film of oil has a minimum thickness of between 0.3 and 1 mm over the central rounded portion (12) of the cooking surface (10a). The quantity of oil (9) is obtained by analyzing the mass properties of the object created using CAD.

The predetermined cooking temperature is that of potatoes, to the extent that cooking this food requires the use of fat in order to properly cook it and improve its organoleptic qualities. Thus, the potatoes are cut into rounds or in pieces, or even whole, depending on their size, to make a sautéed potatoes recipe commonly eaten in households. For example, 800 g of potatoes are used. This recipe requires the use of fat appropriate for demonstrating the point of the method described in the invention. Indeed, for optimal success, this recipe requires cooking potatoes by pan-frying them, with a thin film of fat to remove the pockets of air between the bottom of the frying pan and the potatoes, as these pockets of air thermally insulate a portion of the food from the cooking surface. Moreover, this cooking choice more quickly conducts the heat from the cooking surface to the potatoes, while avoiding any disparity in cooking these potatoes.

In addition, for implementing the method described in the invention and this sautéed potato recipe, the fat used is peanut oil. However, any other cooking oil can be used, and even any other fat that completely or partially liquefies once the predetermined cooking temperature is reached, such as butter or beef fat, for example.

Figure 5:
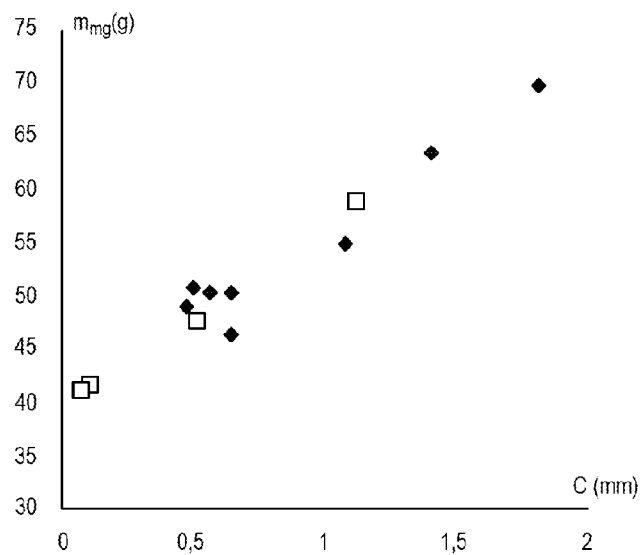
FIG. 5 presents a graph of the mass of oil necessary to cover the bottom surface, as a function of the concavity of the cooking utensil.

Thus, for a sample group of cooking utensils (11) tested, particularly frying pans, of which the concavity of the bottom (10) changes when the temperature of the cooking surface reaches 180° C., the graph in FIG. 5 is obtained, which illustrates the mass of oil used ($m_{mg}$) that was necessary to cover the bottom (10) of the frying pan (11) as a function of the concavity (C) of said bottom. It is therefore clear that the mass of oil used ($m_{mg}$) ranges between approximately 40 g and 70 g for a concavity (C) of the bottom (10), which ranges between approximately 0.1 mm, which is slight concavity, and 2 mm, which is significant concavity.

These test were performed with Tefal™ Grand Chef frying pans measuring 26 cm in diameter and 190 mm±1 mm in span diameter. This is a concavity-to-span diameter ratio of between 0.0005 and 0.01.

For the sample group of frying pans chosen for testing, the mass of the frying man ($m_{uc}$) and the mass of the oil used ($m_{mg}$) were measured. An identical mass of raw potatoes ($m_{ac}$), from the some place of origin, were also used for each cooking. These mass measurements were taken using a weighing device known to the expert in the field.

The method includes a step (c), which consists of potato cooking tests, with the sample group of frying pans and the mass of oil ($m_{mg}$) necessary to cover the cooking surface (10a) when hot, ready for cooking this food. Once cooking is complete, the prepared sautéed potatoes are removed and weighed. Thus a mass ($m_{ap}$) is obtained for the prepared potatoes for the sample group of frying pans. Likewise, the mass ($m_{uc+rmg}$) of the frying pan and the residual oil in the frying pan are measured once the prepared sautéed potatoes are removed from that frying pan.

These tests show that, the greater the mass of oil used ($m_{mg}$) in the frying pan, the greater the mass of oil absorbed ($m_{mga}$) in the prepared sautéed potatoes. The maximum amount of oil absorbed by the potatoes during cooking is variable. That amount depends on the variety of potatoes and their water content, among other factors. This is why it is important to use the same potatoes for all the tests with the sample group of frying pans.

The method includes a step (d) that consists of determining the percentage of fat with respect to the dry matter of the potatoes $Tx_{MG/MS}$ for the sample group of frying pans.

First, from the previous measurements, the mass of oil absorbed ($m_{mga}$) by the sautéed potatoes prepared with the sample group of frying pans is deduced. The following formula is used: $m_{mga}=m_{mg}-(m_{uc+rmg}-m_{uc})$.

Figure 6:
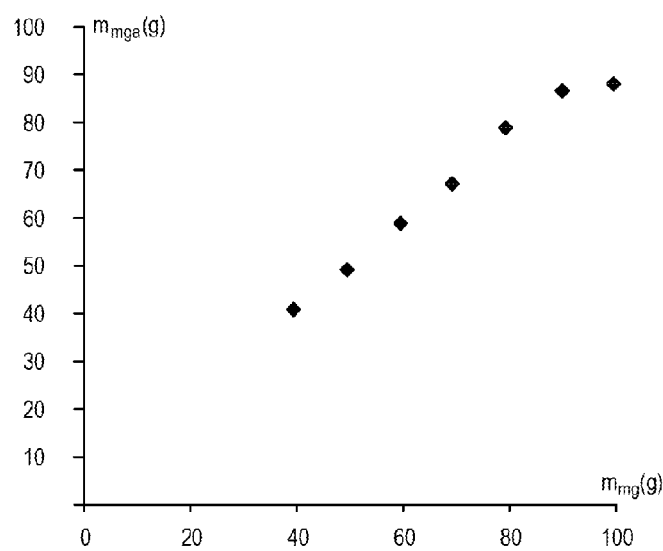
FIG. 6 presents a graph of the mass of oil absorbed by the cooked food, as a function of the mass of oil used.

The tests performed with the sample group of frying pans show that the mass of oil absorbed ($m_{mga}$) by the sautéed potatoes increases with the mass of oil used ($m_{mg}$), as illustrated in FIG. 6.

The percentage of fat with respect to the dry matter of the potatoes $Tx_{MG/MS}$ is then determined using the following formula: $Tx_{MG/MS}=m_{mga}/m_{ac}/Tx_{MS}$, where $Tx_{MS}$ is the percentage of dry matter of the potatoes.

This percentage of dry matter of the potatoes is determined as follows. For a sample of potatoes identical to the ones used for the tests, and, for an identical mass of raw potatoes ($m_{ac}$), they are placed in a drying oven at 100° C. for 24 hours, and then the mass of the potato sample is measured after drying ($m_{acs}$). The percentage of dry matter is thus calculated: $Tx_{MS}=m_{ac}/m_{acs}$.

The method includes a step consisting of measuring the deformation of the bottom of the hot frying pan, specifically at the cooking temperature predetermined for cooking a food.

This measurement of the deformation of the hot frying pan is taken on a sample group of frying pans with similar dimensions, but technically different characteristics that will consequently accentuate to a greater or lesser extent said deformation of the bottom of the hot frying pan.

The measurement of the deformation when hot is taken using the method defined in Standard XP D21-503, or even using any other method known to the expert in the field.

Figure 7:
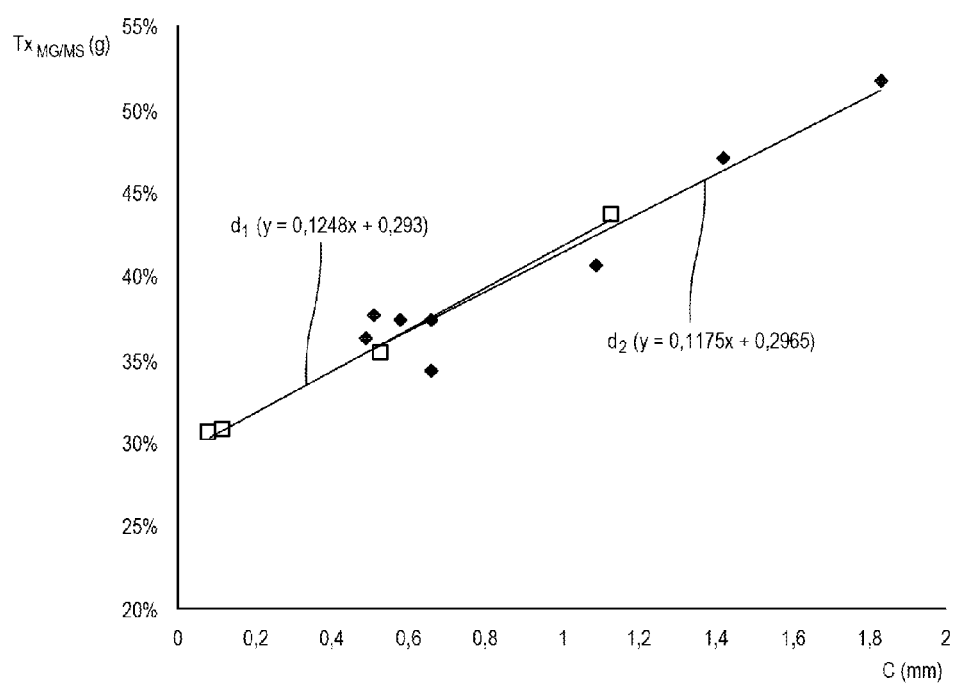
FIG. 7 presents a graph of the percentage of fat absorbed with respect to the dry matter of the food, as a function of the concavity of the cooking utensil.

From these tests, and, based on the measurements and calculations made, one obtains the graph in FIG. 7, which illustrates the percentage of fat with respect to the dry matter of the potatoes ($Tx_{MG/MS}$) as a function of the concavity (C) of the bottom (10) for the sample group of frying pans (11) tested. This graph produces two mean lines (d1, d2) with the equation for d1 being y=0.1248x+0.293, and for d2 being y=0.1175x+0.2965. This is a mean line with a slope of roughly 12%.

Thus, the testing shows, for the sample group of frying pans in question and for cooking sautéed potatoes, that a decrease of 1 mm in the concavity when hot results in a 12% decrease in the percentage of fat in the prepared food.

In one variant, the percentage of fat with respect to the dry matter of the potatoes ($Tx_{MG/MS}$) can also be related to the mass ($m_{ap}$) for the prepared potatoes. However, the comparison of the percentage of cooking fat obtained in two different frying pans becomes problematic. Indeed, one must ensure that both pans of prepared food have been cooked to the same degree of completeness in order to be sure that the water lost during cooking has remained the same.

The method described in the invention can obviously be implemented with a sample group of frying pans of differing diameters and for preparing different foods. The final results being similar to those obtained with the tests described above, knowing that, in any case, these tests show that the quantity of fat absorbed by the cooked food decreases when the concavity of the bottom of the frying pan decreases, all other cooking conditions being kept the same so as not to change the organoleptic quality of the prepared food.

The method described in the invention can be applied by utensil manufacturers to certify the quality of cooking utensils for cooking food, such as frying pans, sauté pans or others sold on the market. Indeed, the method described in the invention helps to optimize a nutritional gain by controlling the concavity of the bottom of hot cooking utensils, which manufacturers will seek to attain for a favorable evaluation of their products, by means of said method.

The invention claimed is:

1. Method of determining a performance index of a cooking utensil for a predetermined cooking temperature, with the aim of assessing nutritional gain, said cooking utensil comprising a bottom with a cooking surface, said method comprising the following steps:
   a) Bringing the cooking surface to said predetermined cooking temperature using a heating means, the heating of the surface resulting in a deformation of the bottom;
   b) Determining a minimum quantity of fat necessary to cover the entire cooking surface of the bottom, deformed in this way, at said predetermined cooking temperature by pouring in the minimum quantity of fat necessary to cover the entire cooking surface or by calculating said minimum quantity of fat necessary to cover the entire cooking surface by recreating the cooking utensil, deformed in this way, using a computer equipped with computer assisted design software, said minimum quantity of fat making it possible to determine the performance index of the cooking utensil for a predetermined cooking temperature,
   wherein, in the performance of step b), the steps below are followed:
   i. a quantity of fat corresponding to a liquid volume of 1 mm thick and a surface area equal to a flat disc equivalent to the cooking surface is poured in,
   ii. the fat is spread over the cooking surface of the bottom at the predetermined cooking temperature,
   iii. a residual cooking surface not covered by the fat is measured, and a quantity of fat corresponding to a liquid volume of 1 mm thick and a surface area equal to a flat disc equivalent to the residual cooking surface is poured in,
   iv. steps ii and iii are repeated until the cooking surface of the bottom of the cooking utensil is completely covered.

2. Method described in claim 1, wherein, in the performance of step (b), the cooking utensil is created using computer assisted design, the minimum quantity of fat necessary to cover the bottom of the cooking utensil is graphically represented, and then the mass properties of the object created using computer assisted design are analyzed in order to calculate said quantity of fat necessary for cooking.

3. Method described in claim 1, wherein in step (a), the predetermined cooking temperature is that of potatoes, on the order of 180 to 200° C.

4. Method described in claim 1, wherein in step (b), the fat is cooking oil.

5. Method described in claim 1, further comprising the following steps:
   a) Cooking the food in the cooking utensil and quantifying the fat absorbed by the cooked food;
   b) Determining the percentage of fat absorbed with respect to the dry matter of the cooked food.

6. Method described in claim 5, wherein to perform step (c):
   1. The mass ($m_{uc}$) of the cooking utensil (11) is measured;
   2. The mass ($m_{mg}$) of the fat used (9) is measured;
   3. The mass ($m_{ac}$) of the raw food is measured;
   4. The mass ($m_{ap}$) of the prepared food is measured;
   5. The mass ($m_{uc+rmg}$) of the cooking utensil and of the residual fat is measured once the food is prepared and removed from the cooking utensil, and 6. The mass ($m_{mga}$) of the fat absorbed by the prepared food is deduced.

7. Method described in claim 6, wherein the percentage of fat absorbed with respect to the dry matter of the cooked food is determined using the formula $Tx_{mga/ms} = m_{mga}/m_{ac}/Tx_{ms}$, where $Tx_{ms}$ is the percentage of dry matter of the food and is calculated as $Tx_{ms} = m_{ac}/m_{acs}$ where $m_{acs}$ is a mass of the food after drying.

8. Method described in claim 7, comprising a step to measure the deformation of the bottom of the cooking utensil at the predetermined cooking temperature after step (a), and in that in step (d) the percentage of fat absorbed with respect to the dry matter of the cooked food is associated with the deformation of the cooking utensil.

9. Method described in claim 8, wherein the measurement of the deformation of the bottom of the cooking utensil at the predetermined cooking temperature is taken in accordance with Standard XP D21-503.

10. Method described in claim 1, wherein the cooking utensil is a frying pan.

11. Method described in claim 9, wherein the cooking utensil is a frying pan.

\* \* \* \* \*

UNITED STATES PATENT AND TRADEMARK OFFICE
CERTIFICATE OF CORRECTION

PATENT NO.        : 9,995,721 B2  
APPLICATION NO.   : 14/778365  
DATED             : June 12, 2018  
INVENTOR(S)       : Céline Hofleitner et al.

Page 1 of 1

It is certified that error appears in the above-identified patent and that said Letters Patent is hereby corrected as shown below:

On the Title Page

Column 2, Item (57) ABSTRACT, Line 3, delete "with," and insert -- with --

Signed and Sealed this  
Sixteenth Day of April, 2019

Andrei Iancu  
*Director of the United States Patent and Trademark Office*